United States Patent [19]

Tahara et al.

[11] Patent Number: 4,645,862
[45] Date of Patent: Feb. 24, 1987

[54] ISOPRENYLAMINE DERIVATIVES

[75] Inventors: Yoshiyuki Tahara, Saitama; Yasuhiro Komatsu, Niiza; Hiroyasu Koyama, Ageo; Reiko Kubota, Hasuda; Teruhito Yamaguchi, Tokyo; Toshihiro Takahashi, Ohi, all of Japan

[73] Assignee: Nisshin Flour Milling Co., Ltd., Japan

[21] Appl. No.: 723,082

[22] Filed: Apr. 15, 1985

Related U.S. Application Data

[63] Continuation of Ser. No. 377,580, May 12, 1982, abandoned.

[30] Foreign Application Priority Data

May 18, 1981 [JP] Japan ................................. 56-76158

[51] Int. Cl.$^4$ ..................... C07C 87/28; C07C 87/48
[52] U.S. Cl. ................................. 564/370; 544/392; 544/401; 544/402; 544/403; 564/363; 564/367; 564/368; 564/369; 564/371; 564/374; 564/384; 564/509

[58] Field of Search ............... 564/367, 368, 370, 371

[56] References Cited

U.S. PATENT DOCUMENTS 4,514,573  4/1985  Tahara et al. ................. 564/387

Primary Examiner—Robert V. Hines
Attorney, Agent, or Firm—Abelman Frayne Rezac & Schwab

[57] ABSTRACT

Compounds of the formula

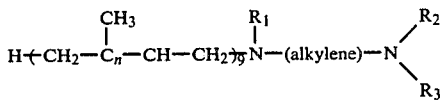

wherein $R_1$ and $R_3$ each is benzyl or substituted with up to 3 methoxy groups, $R_2$ is a hydrogen atom and (alkylene) is lower alkyl and the compounds are useful for controlling viral infections.

3 Claims, No Drawings

ISOPRENYLAMINE DERIVATIVES

This is a continuation of U.S. patent application Ser. No. 377,580, filed May 12, 1982, and abandoned.

This invention relates to new isoprenylamine derivatives and acid addition salts thereof, which are useful for controlling virus infection of vertebrate animals.

There are known heretofore various substances, which have been decided to have preventive or alleviative effects on diseases caused by virus whose host is a vertebrate animal, or which have been recognized to be capable of alleviating symptoms of the diseases by significantly enhancing antibody activity in the animal. Antivirotics reported so far include interferon, substances capable of inducing interferon, i.e. inducers (interferon inducers), and synthetic substances, such as amantadine hydrochloride or methisazone, which directly exert inhibitory effect on virus propagation. Interferon is glycoprotein having antiviral and antitumor activities, said glycoprotein being produced in situ by cells of a vertebrate animal when the cells are infected with virus, and has been known to be effective in therapy of infectious viral disease as well as of cancer. Known inducers, which induce interferon in vertebrate animals through a process other than virus infection, include natural high molecular substances such as double strand ribonucleic acid of bacteriophage of a certain species, or synthetic high molecular substances such as double strand ribonucleic acid, typical of which is polyinosinic acid-polycytidylic acid, or low molecular inducers such as tilorone.

In the production of interferon, however, there is involved a problem how to carry out purification thereof, and in fact, no economical process for the production thereof has not been established yet. On the other hand, conventional interferon inducers have not been put to practical use mainly because of toxicity thereof. Synthetic antiviral agents which directly exert inhibitory effect on virus propagation, which are commercially available at present, have a rather narrow range of virus-infected diseases which are curable by administration of said agents, and thus the advent of novel synthetic antiviral agents is earnestly desired. Taking such circumstances into consideration, the present inventors extensively conducted studies in finding compounds capable of producing interferon of high potency and, moreover, having antiviral activity on the biological level, and as the result they have eventually found that compounds represented by the general formula (I) and acid addition salts thereof show excellent interferon-inducing ability and, at the same time, demonstrate excellent antiviral activity even in the biological test.

Thus, the present invention is to provide a new class of an isoprenylamine derivative represented by the following general formula

(I)

wherein at least one or two of $R_1$, $R_2$ and $R_3$ represent

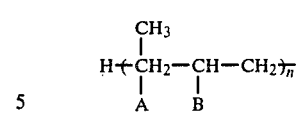

(in which n represents an integer of 2 to 10, and A and B are individually hydrogen atoms or may jointly form a linking group, and when n is 4, A and B may be a combination of the aforesaid two cases), or $R_2$ and $R_3$ may, together with the adjacent nitrogen atom, form a 1,7,10,16-tetraoxa-4,13-diazacyclo-octadecane ring, and the remainder of $R_1$, $R_2$ and $R_3$ may be hydroxyethyl, phenyl, benzyl, nucleically substituted benzyl, phenethyl, nucleically substituted phenethyl, α-hydroxyphenethyl or phenylbutyl or a group of the formula

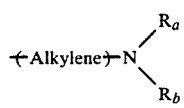

(in which "Alkylene" is a lower alkylene chain which may be hydroxy-substituted, $R_a$ and $R_b$, which may be the same of different, represent hydrogen, hydroxyethyl, lower alkyl or optionally nucleically substituted benzyl, or $R_a$ and $R_b$ may be a divalent residue which, together with the adjacent nitrogen atom, form N'-hydroxy-(substituted piperazine), and acid addition salts thereof. For the production of isoprenylamine derivatives represented by the above-mentioned general formula (I) and acid addition salts thereof, there may be adopted the known procedure in which isoprenyl alcohol (e.g. decaprenol, solanesol, phytol or geraniol) represented by the general formula

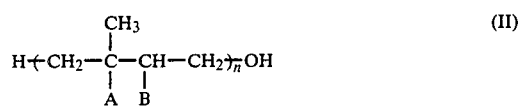

wherein A, B and n are as defined above, is first converted into a corresponding halide (e.g. geranyl bromide, solanesyl bromide, phytyl bromide or decaprenyl bromide) or arylsulfonic acid ester (e.g. decaprenyl tosylate or solanesyl tosylate) and the resulting halide or ester is then allowed to react in the presence or absence of a base with a compound represented by the general formula

wherein $R_2$ and $R_3$ are as defined above. This reaction is usually carried out in an organic solvent. Preferably usable as organic solvents in the reaction one common solvents such as methanol, ethanol, chloroform, isopropyl ether, benzene and ethyl acetate. In the practice of the above-mentioned reaction, it is preferable that a large excess of an amino compound represented by the general formula (III) is used, or the reaction is carried out at a temperature ranging from room temperature up to 100° C. in the presence of a base (e.g. sodium hydroxide, potassium hydroxide, sodium carbonate or potassium carbonate). After the completion of the reaction, a desired isoprenylamine derivative can be obtained by treating the resultant reaction liquid according to usual isolation and purification procedures such as extraction, concentration, column chromatography, crystallization and the like.

For the production of compounds represented by the general formula (I), which compounds contain a primary or secondary amino group, there may also be adopted another process in which a compound represented by the general formula $$R'COX \quad \text{(IV)}$$

wherein R' is a phenyl, substituted phenyl or benzyl group and X is halogen, is allowed to undergo reaction at 0°–50° C. in the presence of a base (such tertiary amine, e.g. pyridine and triethylamine) to obtain an acylated compound and the thus obtained N-acylated compound is then reduced with a reducing agent (e.g. lithium aluminum hydride). This reduction reaction is suitably carried out at a temperature ranging from room temperature up to 60° C. in such organic solvent as tetrahydrofuran or ether. After completion of the reaction, a desired isoprenylamine derivative can be produced by treating the resultant reaction liquid according to usual isolation and purification procedures such as extraction, concentration, column chromatography, crystallization and the like.

Further, of the compounds represented by the general formula (I), those in which one or two of $R_1$, $R_2$ and $R_3$ represent a group

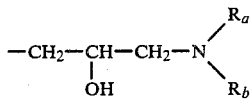

wherein $R_a$ and $R_b$ are as defined above can be produced even by the following process. That is, such compounds as referred to above are produced by reacting the aforementioned halide or arylsulfonic acid ester in the presence or absence of a base with a compound represented by the general formula $$H_2N-R' \quad \text{(V)}$$

wherein R' represents a substituted or unsubstituted benzyl or substituted or unsubstituted phenethyl group, to obtain a compound represented by the general formula

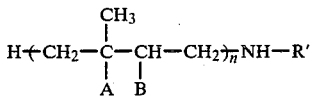

wherein R', A, B and n are as defined above, then reacting the resulting compound in the presence or absence of a base with a compound represented by the general formula

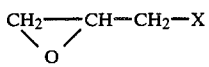

wherein X represents halogen, to obtain a compound represented by the general formula

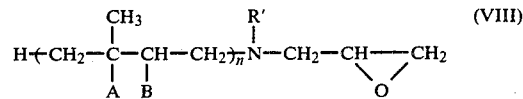

wherein A, B, n and R' are as defined above, and then reacting the resulting compound with an amino compound represented by the general formula

wherein $R_a$ and $R_b$ are as defined above. The above-mentioned reaction, in which the compound represented by the general formula (XI) is used as a reactant, is preferably carried out by using a large excess of said compound in an alcoholic solvent (e.g. methanol or ethanol) or in the absence of any solvent. This reaction is suitably carried out at a temperature ranging from room temperature up to 100° C. After the completion of the reaction, a desired isoprenylamine derivative can be obtained by treating the resultant reaction liquid according to usual isolation and purification procedures such as extraction, concentration, column chromatography, crystallization and the like. An acid addition salt of the isoprenylamine derivative thus obtained can be obtained by mixing said derivative in an appropriate solvent (e.g. acetone or ethyl acetate) with a desired acid to form a salt and applying such means as concentration, crystallization or the like to the salt. The acid addition salts suitable for use as medicines include, for example, those with hydrochloric acid, acetic acid, citric acid, fumaric acid, lactic acid and the like.

Illustrated below are preparative examples of isoprenylamine derivatives of the present invention.

PREPARATIVE EXAMPLE 1

N-decaprenyl-N-(2-hydroxy-2-phenylethyl)ethanolamine hydrochloride

To an ethanol solution (100 ml) containing N-(2-hydroxy-2-phenylethyl)ethanolamine (16.4 g) an isopropyl ether solution (100 ml) containing decaprenyl bromide (20 g) was added dropwise at room temperature for 1 hour with stirring. The mixture was stirred at room temperature for 3 hours and heated under reflux for additional 1 hour with stirring. After cooling, the reaction liquid was charged with a 5% aqueous sodium hydroxide solution (100 ml) and extracted with isopropyl ether. The extract was washed with water and saturated saline, dried over anhydrous sodium sulfate and then concentrated under reduced pressure. The concentrate (18.1 g) was chromatographed with a chloroform-ethyl acetate mixture over a column packed with silica gel (200 g) to obtain an oily product (15.3 g). This oily product was dissolved in aceton (50 ml), weakly acidified with an ether solution of hydrogen chloride and allowed to stand overnight in a refrigerator. The crystallized mass was separated by filtration and dried to obtain N-decaprenyl-N-(2-hydroxy-2-phenylethyl)ethanolamine hydrochloride (13.6 g) represented by the formula mentioned below.

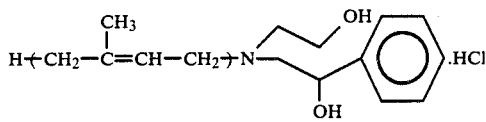

Given below are measured values of physical properties of the title compound.

Melting point: 58.6°–59.9° C.

N.M.R. (value in CDCl$_3$) (Free base):

| | |
|---|---|
| 7.30 | (5H, s) |
| 4.93–5.32 | (10H, br) |
| 4.70 | (1H, t, J = 6 Hz) |
| 3.65 | (2H, t, J = 6 Hz) |
| 3.23 | (2H, d, J = 7 Hz) |
| 2.50–2.92 | (4H, m) |
| 2.00 | (36H, br-s) |
| 1.59 | (33H, s) |

Elementary analysis (as $C_{60}H_{95}NO_2 \cdot HCl \cdot \frac{1}{2}H_2O$):

| | Calcd. | Found |
|---|---|---|
| C (%) | 79.37 | 79.58 |
| H (%) | 10.76 | 10.79 |
| N (%) | 1.54 | 1.53 |

PREPARATIVE EXAMPLE 2

N-(3,4-dimethoxybenzyl)disolanesylamine

To an ethanol solution (100 ml) containing 3,4-dimethoxybenzylamine (25 g) an isopropyl ether solution (100 ml) containing solanesyl bromide (30 g) was added dropwise at room temperature over a period of 1 hour with stirring. The mixture was stirred at room temperature for 3 hours and heated under reflux for additional 1 hour with stirring. After cooling, the reaction liquid was charged with a 5% aqueous sodium hydroxide solution (100 ml) and extracted with isopropyl ether. The extract was washed with water and saturated saline, dried over anhydrous sodium sulfate and concentrated under reduced pressure. The concentrate (33.6 g) was chromatographed with a chloroform-ethyl acetate solution over a column packed with silica gel (350 g) to obtain N-(3,4-dimethoxybenzyl)disolanesylamine (7.1 g) represented by the formula mentioned below.

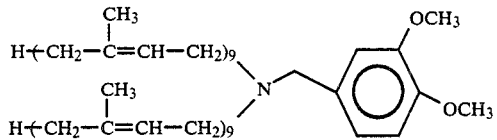

Given below are measured values of physical properties of the title compound.

$n_D^{21.5} = 1.5181$

N.M.R. (δvalue in CDCl$_3$):

| | |
|---|---|
| 6.71–6.92 | (3H, m) |
| 4.9–5.3 | (18H, br) |
| 3.83 | (6H, s) |
| 3.46 | (2H, s) |
| 3.00 | (4H, d, J = 7 Hz) |
| 2.02 | (64H, br) |

-continued

| | |
|---|---|
| 1.60 | (60H, s) |

Elementary analysis (as $C_{99}H_{157}NO_2$):

| | Calcd. | Found |
|---|---|---|
| C (%) | 85.34 | 85.59 |
| H (%) | 11.36 | 11.51 |
| N (%) | 1.01 | 0.97 |

PREPARATIVE EXAMPLE 3

N,N-di(3-aminopropyl)decaprenylamine trihydrochloride

To a chloroform solution (100 ml) containing dipropylenetriamine (50 g) a chloroform solution (100 ml) containing decaprenyl bromide (40 g) was added dropwise at room temperature over a period of 1 hour with stirring. The resultant mixture was stirred at room temperature for additional 3 hours. The reaction liquid was concentrated under reduced pressure to remove the chloroform therefrom and the resulting concentrate was extracted with ethyl acetate. The extract was washed with water and saturate saline, dried over anhydrous sodium sulfate and concentrated under reduced pressure to obtain a concentrate (48.1 g). The concentrate was then dissolved in isopropyl ether (100 ml) and charged with sodium carbonate (20 g). To the resulting mixture, while cooling with ice-water, trifluoroacetic anhydride (30 ml) was added dropwise over a peiord of 1 hour with stirring, and the mixture was stirred for additional 3 hours while cooling. After the completion for the reaction, the reaction liquid was filtered to separate insolubles and the filtrate was concentrated under reduced pressure. The concentrate was charged with benzene (about 50 ml) and then concentrated under reduced pressure. The concentrate (49.3 g) was chromatographed with a benzene-ethyl acetate mixture over a column packed with silica gel (500 g) to obtain N,N-di(3-trifluoroacetylaminopropyl)decaprenylamine (10.1 g), which was then charged with an ethanol solution (100 ml) of a 10% potassium hydroxide and heated under reflux for 1 hour. After cooling, the reaction liquid was charged with water (300 ml) and then extracted with ethyl acetate. The extract was washed with water and saturated saline, dried over anhydrous sodium sulfate and concentrated under reduced pressre. The concentrate (8.9 g) was dissolved in acetone (50 ml), charged with a hydrogen chloride-ether solution to weakly acidic and then concentrated under reduced pressure to dryness to obtain N,N-di(3-aminopropyl)-decaprenylamine trihydrochloride (9.1 g) represented by the following formula.

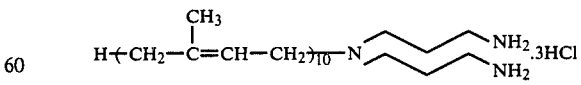

Given below are measured values of physical properties of the tile compound.

Melting point: Caramel-like state.

N.M.R. (δvalue in CDCl$_3$) (Free base):

| | |
|---|---|
| 4.9–5.3 | (10H, br) |

| 3.00 | (2H, d, J = 7 Hz) |
| 2.32–2.86 | (8H, m) |
| 2.02 | (36H, br) |
| 1.61 | (37H, s) |

Elementary analysis (as $C_{56}H_{97}N_3 \cdot 3HCl \cdot H_2O$):

|  | Calcd. | Found |
| --- | --- | --- |
| C (%) | 71.57 | 71.66 |
| H (%) | 10.94 | 10.81 |
| N (%) | 4.47 | 4.13 |

PREPARATIVE EXAMPLE 4

N,N,-di(3-aminopropyl)solanesylamine trihydrochloride

The same procedures as in Preparative Example 3 were carried out for the reaction of solanesyl bromide with dipropylenetriamine thereby to produce N,N-di(3-aminopropyl)solanesylamine trihydrochloride of the following formula.

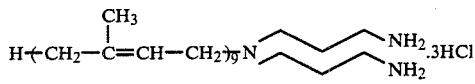

Given below are measured values of physical properties of the title compound.
Melting point: Caramel-like state.
N.M.R. (δvalue in CDCl$_3$) (Free base):

| 4.9–5.3 | (9H, br) |
| 3.05 | (2H, d, J = 7 Hz) |
| 2.33–2.90 | (8H, m) |
| 2.00 | (32H, br) |
| 1.60 | (34H, s) |

Elementary analysis (as $C_{51}H_{89}N_3 \cdot 3HCl \cdot 2H_2O$):

|  | Calcd. | Found |
| --- | --- | --- |
| C (%) | 68.85 | 68.93 |
| H (%) | 10.88 | 10.91 |
| N (%) | 4.72 | 4.51 |

PREPARATIVE EXAMPLE 5

N-solanesyl-N,N'-bis(3,4-dimethoxybenzyl)ethylenediamine dihydrochloride

To an ethanol solution (200 ml) containing ethylenediamine (100 g) an isopropyl ether solution (200 ml) containing solanesyl bromide (89 g) was added dropwise at room temperature over a period of 2.5 hours with stirring. The resulting compound was stirred at room temperature for 3.0 hours and heated under reflux for additional 1 hour with stirring. After cooling, the reaction liquid was charged with a 5% sodium hydroxide (200 ml) and then extracted with isopropyl ether. The extract was washed with water and saturated saline, over anhydrous sodium sulfate and then concentrated under reduced pressure. The concentrate (93.2 g) was dissolved in acetone (500 ml), charged with an ether solution of hydrogen chloride to weakly acidic and then allowed to stand at room temperature overnight. The crystallized mass was separated by filtration and dired to obtain crude N-solanesyletheylenediamine hydrochloride (47.1 g). To a chlorofrm solution (100 ml) containing the thus obtained crude N-solanesylethylenediamine hydrochloride (23.5 g) was added pyridine (25 ml) and thereafter was added dropwise at room temperature a chloroform solution (100 ml) containing 3,4-dimethoxybenzoyl chloride (15.0 g) over a period of 1 hour with stirring, the resulting mixture was stirred at room temperature for additional 2.0 hours. The reaction liquid was extracted with isopropyl ether, and the extract washed with water, 5% hydrochloric acid, 5% aqueous sodium hydrogen carbonate solution and saturated saline, dried over anhydrous sodium sulfate and then concentrated under reduced pressure. The concentrate (31.3 g) was chromatographed with a chloroform-ethyl acetate mixture over a column packed with silica gel (350 g) to obtain N-solanesyl-N,N'-bis(3,4-dimethoxybenzoyl)ethylenediamine (28.3 g). To an anhydrous diethyl ether solution (200 ml) containing N-solanesyl-N,N'-bis(3,4-dimethoxybenzoyl)ethylenediamine was added in small portions at room temperature lithium aluminum hydride (3.8 g) with stirring. The resulting mixture was stirred at room temperature for 1 hour and then heated under reflux for 3 hours with stirring. After decomposing unaltered lithium aluminum hydrided with water, the reaction liquid was extracted with isopropyl ether. The extract was washed with water and saturated saline, dried over anhydrous sodium sulfate and concentrated under reduced pressure. The concentrate (28.6 g) was chromatographed with a chloroform-ethyl acetate mixture over a column packed with silica gel (300 g) to obtain an oily product (17.5 g). This oily product was dissolved in acetone (500 ml), charged with an ether solution of hydrogen chloride to weakly acidic and then allowed to stand in a refrigerator overnight. The crystallized mass was separated by filtration and then dried to obtain N-solanesyl-N,N'-bis(3,4-dimethoxybenzyl)ethylenediamine dihydrochloride (10.7 g) represented by the following formula.

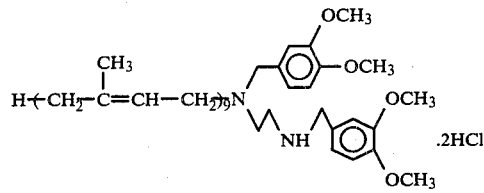

Given below are measured values of physical properties of the title compound.

$n_D^{17.5} = 1.5238$

N.M.R. (δvalue in CDCl$_3$) (Free base):

| 6.67–6.97 | (6H, br) |
| 4.82–5.51 | (9H, br) |
| 3.83 | (12H, s) |
| 3.63 | (2H, s) |
| 3.48 | (2H, s) |
| 3.05 | (2H, d, J = 7 Hz) |
| 2.55 | (4H, br) |
| 1.98 | (32H, br) |
| 1.58 | (30H, s) |

Elementary analysis (as $C_{65}H_{100}N_2O_4 \cdot 2HCl \cdot H_2O$):

| | Calcd. | Found |
|---|---|---|
| C (%) | 73.34 | 73.67 |
| H (%) | 9.85 | 9.91 |
| N (%) | 2.63 | 2.56 |

PREPARATIVE EXAMPLE 6

N-solanesyl-N,N''-dibenzylethylenediamine dihydrochloride

The same procedures as in Preparative Example 5 were carried out for the reaction of solanesyl bromide with ethylenediamine to obtain N-solanesylethylenediamine and then for the reaction of N-solanesylethylenediamine with benzoyl chloride to obtain N-solanesyl-N,N'-dibenzoylethylenediamine which was then reduced with lithium aluminum hydride to obtain N-solanesyl-N,N'-dibenzylethylenediamine dihydrochloride represented by the following formula.

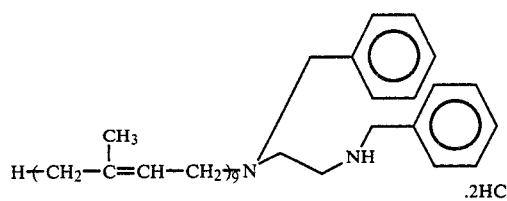

Given below are measured values of physical properties of the title compound.

$n_D^{19} = 1.5311$

N.M.R. (δ value in CDCl) (Free base):

| 7.23 | (10H, s) |
|---|---|
| 4.9–5.3 | (9H, br) |
| 3.65 | (2H, s) |
| 3.50 | (2H, s) |
| 3.00 | (2H, d, J = 7 Hz) |
| 2.62 | (4H, br-s) |
| 2.00 | (32H, br) |
| 1.60 | (30H, s) |

Elementary analysis (as $C_{61}H_{92}N_2 \cdot 2HCl \cdot H_2O$):

| | Calcd. | Found |
|---|---|---|
| C (%) | 77.58 | 77.72 |
| H (%) | 10.25 | 10.05 |
| N (%) | 2.97 | 2.86 |

PREPARATIVE EXAMPLE 7

N-solanesyl-N,N'-bis(3,4,5-trimethoxybenzyl)-N'-(3,4-dimethoxybenzyl)ethylenediamine dihydrochloride The same procedures as in Preparative Example 5 were carried out for the reaction of solanesyl bromide with ethylenediamine to obtain N-solanesylethylenediamine. Subsequently, after the reaction of N-solanesylethylenediamine with 3,4,5-trimethoxybenzoyl chloride, the reaction product was reduced with aluminum lithium hydride to obtain N-solanesyl-N,N'-bis(3,4,5-trimethoxybenzyl)ethylenediamine. Further, after the reaction of N-solanesyl-N,N'-bis(3,4,5-trimethoxybenzyl)ethylenediamine with 3,4-dimethoxybenzoyl chloride, the reaction product was reduced with lithium aluminum hydride to obtain N-solanesyl-N,N'-bis(3,4,5-trimethoxybenzyl)-N'-(3,4-dimethoxybenzyl)ethylenediamine dihydrochloride represented by the following formula.

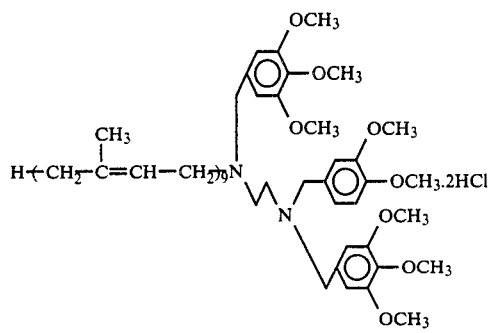

Given below are measured values of physical properties of the title compound.

$n_D^{17.5} = 1.5263$

N.M.R. (δ value in CDCl₃) (Free base):

| 6.45–6.95 | (7H, m) |
|---|---|
| 4.83–5.43 | (9H, br) |
| 3.80, 3.73 | (24H, s) |
| 3.50 | (6H, s) |
| 3.02 | (2H, d, J = 7 Hz) |
| 1.99 | (32H, br) |
| 1.60 | (30H, s) |

Elementary analysis (as $C_{76}H_{114}N_2O_8 \cdot 2HCl \cdot H_2O$):

| | Calcd. | Found |
|---|---|---|
| C (%) | 71.61 | 71.54 |
| H (%) | 9.33 | 9.21 |
| N (%) | 2.20 | 2.13 |

PREPARATIVE EXAMPLE 8

4-[3-(N-solanesylphenythylamino)-2-hydroxypropyl]-1-piperazineethanol trihydrochloride To an ethanol solution (150 ml) containing phenethylamine (40 g) an isopropyl ether solution (150 ml) containing solanesyl bromide (50 g) was added dropwise at room temperature over a period of 1 hour with stirring. The resulting mixture was stirred at room temperature for 3 hours and then heated under reflux for additional 1 hour with stirring. After cooling, the reaction liquid was charged with a 5% aqueous sodium hydroxide solution (150 ml) and then extracted with isopropyl ether. The extract was washed with water and saturated saline, dried over anhydrous sodium sulfate and then concentrated under reduced pressure. The concentrate (51.8 g) was chromatographed with a chloroform-ethyl acetate mixture over a column packed with silica gel (550 g) to obtain an oily N-phenethyl solanesylamine (31.3 g). The thus obtained N-phenethyl solanesylamine (31.3 g) and an ethanol solution (100 ml) containing epichlorohydrin (30 ml) and triethylamine (30 ml) were heated under reflux for 2 hours with stirring. The reaction liquid was extracted with isopropyl ether, washed with water and saturated saline, dried over anhydrous sodium sulfate and the concentrated under reduced pressure to obtain a concentrate (31.9 g). This concentrate (9.0 g) and an ethanol solution (50 ml) containing 1-piperazine ethanol (10 g) were heated under reflux for 5 hours with stirring. After cooling, the reaction liquid was charged with water (200 ml) and then extracted with isopropyl ether. The extract was washed with water and saturated saline, dried over anhydrous sodium sulfate and then concentrated under reduced pressure. The concentrate (10.9 g) was chromatographed with a chloroform-methanol mixture over a column packed with silica gel (150 g) to obtain an oily product (6.1 g). This oily product was dissolved in acetone (40 ml), charged with a hydrogen chloride ether solution to weakly acidic and then allowed to stand at room temperature overnight. The crystallized mass was separated by filtration and then dried to obtain 4-[3(N-solanesylphenethylamino)-2-hydroxypropyl]-1-piperazine ethanol trihydrochloride (4.3 g) represented by the following formula.

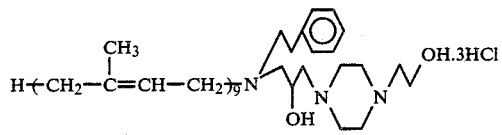

Given below are measured values of physical properties of the title compound.

Melting point: Caramel-like state; 212° C. (Decomposition).

N.M.R. (δ value in CDCl$_3$) (Free Base):

| | |
|---|---|
| 7.14 | (5H, s) |
| 4.82–5.41 | (9H, br) |
| 3.43–3.92 | (3H, m) |
| 2.98–3.40 | (5H, m) |
| 2.40–2.9 | (16H, m) |
| 1.98 | (32H, br) |
| 1.58 | (30H, s) |

Elementary analysis (as $C_{62}H_{101}N_3O_2.3HCl.2H_2O$):

| | Calcd. | Found |
|---|---|---|
| C (%) | 69.86 | 69.50 |
| H (%) | 10.21 | 10.23 |
| N (%) | 3.94 | 3.82 |

PREPARATIVE EXAMPLE 9

The same procedures as in Preparative Example 2 were carried out for the reaction of a compound selected from decaprenyl bromide, solanesyl bromide and geranyl bromide with a compound selected from 1,7,10,16tetraoxa-4,13-diazacyclooctadecane, dibenzylamine, N-benzylethanolamine, 3,4-dimethoxybenzylamine, 4-phenylbutylamine, p-methoxybenzylamine, N-(3-aminopropyl)diethanolamine, 1-benzylpiperazine, p-aminophenethylamine and 4-hydroxy-3-methoxybenzylamine and thereby to produce the below-indicated compounds, the measured values of physical properties of which are listed in Table 1.

In the structural formulas shown in Table 1, "D" represents decaprenyl group, "S" represents solanesyl group, "Phy" represents phytyl group and "Ger" represents geranyl group.

TABLE 1

| Structural formula | Molecular formula | $n_D$/Melting point | N.M.R. (δ value in CDCl₃) Free base | Elementary analysis | | | | | |
|---|---|---|---|---|---|---|---|---|---|
| | | | | Calcd. (%) | | | Found (%) | | |
| | | | | C | H | N | C | H | N |
| (crown ether with NH and D-N) | C₆₂H₁₀₆N₂O₄ | 34.2–35.3° C. | 4.83–5.30(10H,br), 3.43–3.76(16H,br-s), 2.53–3.27(10H,m), 1.98(36H,br-s), 1.60(33H,s) | 78.92 | 11.32 | 2.97 | 78.64 | 11.41 | 2.69 |
| (dibenzyl amine S—N) | C₅₉H₈₇N.HCl.½H₂O | 74.9–78.0° C. | 7.10–7.52(10H,m), 4.9–5.3(9H,br), 3.52(4H,s), 3.00 (2H,d,J=7Hz), 2.00 (32H,br), 1.60(30H,s) | 82.80 | 10.48 | 1.64 | 82.98 | 10.61 | 1.54 |
| (OH dibenzyl S—N).HCl | C₅₅H₈₅NO.HCl | 60.3–61.1° C. | 7.26(5H,s), 4.84–5.46(9H,br), 3.39–3.69(4H,m), 3.07 (2H,d,J=7Hz), 2.61 (2H,t), 2.00(32H,br), 1.60(30H,s) | 81.28 | 10.67 | 1.72 | 80.88 | 10.91 | 1.71 |
| (Phy)₂—N (3,4-dimethoxybenzyl) | C₄₉H₈₉NO₂ | $n_D^{20.5} = 1.4908$ | 6.73–6.96(3H,m), 5.30(2H,t,J=7Hz), 3.86(6H,s), 3.48 (2H,s), 3.02(4H,d,J=7Hz), 0.7–2.2(72H,m) | 81.26 | 12.39 | 1.93 | 81.04 | 12.21 | 1.87 |
| S₂—N (benzyl) | C₁₀₀H₁₅₉N | $n_D^{23.5} = 1.5129$ | 7.16(5H,s), 4.9–5.3(18H,br), 3.00 (4H,d,J=7Hz), 2.3–2.7(4H,m), 1.98 (64H,br), 1.59 (64H,s) | 87.33 | 11.65 | 1.02 | 87.21 | 11.73 | 0.93 |
| (Ger)₂—N (3,4-dimethoxybenzyl) | C₂₉H₄₅NO₂ | | 6.71–6.96(3H,m), 4.9–5.4(2H,m), 3.83(6H,s), 3.46 (2H,s), 3.00(2H, d,J=7Hz), 2.03(8H, br), 1.63(18H,br) | 79.22 | 10.32 | 3.19 | 79.10 | 10.49 | 3.07 |

TABLE 1-continued

| Structural formula | Molecular formula | $n_D$/Melting point | N.M.R. (δ value in CDCl₃) Free base | Elementary analysis | | | | | |
|---|---|---|---|---|---|---|---|---|---|
| | | | | Calcd. (%) | | | Found (%) | | |
| | | | | C | H | N | C | H | N |
| 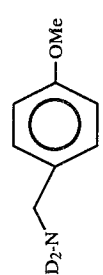 | C₁₀₈H₁₇₁NO | $n_D^{23.3}$ = 1.5199 | 6.76(2H,d,J=8Hz), 7.17(2H,d,J=8Hz), 4.9–5.3(20H,br), 3.75(3H,s), 3.45 (2H,s), 2.98(4H,d, J=7Hz), 2.00(72H, br), 1.60(66H,s) | 78.25 | 10.64 | 3.15 | 78.03 | 10.60 | 3.16 |
| 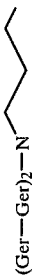 | C₄₇H₈₂N₂O₂·½H₂O | | 3.86–5.42(8H,m), 3.60(4H,t,J=6Hz), 3.03(4H,d,J=7Hz), 2.32–2.77(8H,m), 1.90–2.26(24H,br), 1.60(34H,br-s) | 78.82 | 11.68 | 3.91 | 78.70 | 11.53 | 3.82 |
| 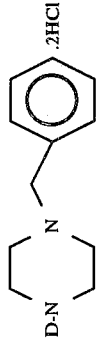 | C₆₁H₉₆N₂·2HCl | 135.4–145.2 (decomp.) | 7.26(5H,s), 4.9–5.3(10H,br), 3.15 (2H,d,J=7Hz), 2.96(2H,d, J=7Hz), 2.46(8H,s), 1.98(36H,br), 1.58 (33H,s) | 78.75 | 10.62 | 3.01 | 78.57 | 10.72 | 2.99 |
| 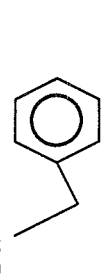 | C₅₉H₉₃NO₂ | 65.2–66.3° C. | 7.27(5H,s), 4.85–5.50(10H,br), 3.4–3.70(4H,m), 3.12(2H, d,J=7Hz), 2.63(2H,t), 2.01(36H,br), 1.57 (30H,s) | 85.13 | 11.26 | 1.68 | 85.15 | 11.38 | 1.69 |
| 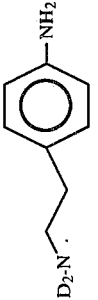 | C₁₀₈H₁₇₂N₂ | $n_D^{27.5}$ = 1.5177 | 6.93(2H,d,J=8Hz), 6.56(2H,d,J=8Hz), 4.9–5.3(20H,br), 3.10(4H,d,J=7Hz), 2.63(4H,br-s), 1.98 (72H,br), 1.58(66H,s) | 86.56 | 11.57 | 1.87 | 86.38 | 11.68 | 1.88 |
| 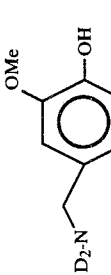 | C₁₀₈H₁₇₁NO₂·2H₂O | $n_D^{27.5}$ = 1.5163 | 6.70–6.95(3H,m), 4.9–5.3(20H,br), 3.83(3H,s), 3.45 (2H,br-s), 3.00(4H, d,J=7Hz), 2.00(36H, br), 1.59(33H,s) | 83.60 | 11.36 | 0.90 | 83.84 | 11.48 | 0.88 |

TABLE 1-continued
| Structural formula | Molecular formula | $n_D$/Melting point | N.M.R. (δ value in CDCl$_3$) Free base | Elementary analysis | | | | | |
| --- | --- | --- | --- | --- | --- | --- | --- | --- | --- |
| | | | | Calcd. (%) | | | Found (%) | | |
| | | | | C | H | N | C | H | N |
| 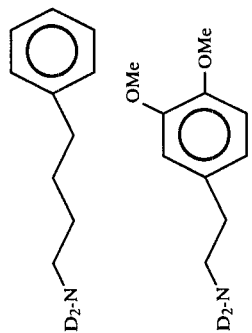 | C$_{110}$H$_{175}$N.H$_2$O | $n_D^{27.5}$ = 1.5140 | 7.10–7.30(5H,m), 4.9–5.3(20H,br), 3.00(4H,d,J=7Hz), 2.3–2.7(4H,m), 1.98 (72H,br), 1.59(70H,s) | 86.37 | 11.66 | 0.92 | 86.11 | 11.57 | 1.04 |
| 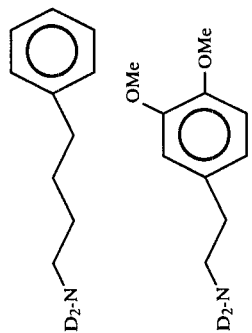 | C$_{110}$H$_{175}$NO$_3$ | $n_D^{27.5}$ = 1.5162 | 6.70(3H,s), 4.9–5.3(20H,br), 3.83 (6H,s), 3.12(4H,d, J=7Hz), 2.50–2.86 (4H,m), 2.00(36H, br), 1.60(33H,s) | 85.59 | 11.43 | 0.91 | 85.47 | 11.31 | 0.90 |

PREPARATIVE EXAMPLE 10

The same procedures as in Preparative Example 8 were carried out for the reaction of N-phenethyl-solanesylamine or N-benzylsolanesylamine with epichlorohydrin, followed by the reaction with tertiary butylamine or diethanolamine, thereby to produce the below-indicated compounds, the measured values of physical properties of which are listed in Table 2.

TABLE 2

| Structural formula | Molecular formula | $n_D$ | N.M.R. ($\delta$ value in CDCl$_3$) Free base | Calc. (%) C H N | Found (%) C H N |
|---|---|---|---|---|---|
| D—N(CH$_2$Ph)(OH)CH$_2$N(CH$_2$CH$_2$OH)$_2$ · 2HCl | C$_{64}$H$_{104}$N$_2$O$_3$·2HCl·H$_2$O | $n_D^{27.5}$ = 1.5009 | 7.24(5H,s), 4.84–5.46(10H,br), 3.5–3.9(7H,br), 3.15 (2H,d,J=7Hz), 2.30–2.87(8H,m), 4.25–4.72(2H,br), 1.98 (36H,br), 1.58(33H,s) | 73.88 10.46 2.69 | 73.85 10.22 2.50 |
| D—N(CH$_2$Ph)(OH)CH$_2$NH—tBu · 2HCl | C$_{64}$H$_{102}$N$_2$O·2HCl·H$_2$O | $n_D^{27.5}$ = 1.5306 | 7.25(5H,s), 4.85–5.48(10H,br), 3.5–3.9(3H,m), 3.13(2H, d,J=7Hz), 2.30–2.87 (4H,m), 1.58(36H,br), 1.58(33H,s), 1.05 (9H,s) | 76.38 10.62 2.78 | 76.46 10.38 2.59 |
| S—N(CH$_2$Ph)(OH)CH$_2$NH—tBu · 2HCl | C$_{60}$H$_{98}$N$_2$O·2HCl·H$_2$O | $n_D^{22.0}$ = 1.4802 | 7.20(5H,s), 4.85–5.46(br,9H), 3.52–3.83(m,1H), 3.16(2H, d,J=7Hz), 2.4–2.90 (m,9H), 2.00(br,32H), 1.58(s,30H), 1.08 (19H,s) | 75.51 10.77 2.94 | 75.39 10.83 2.82 |

Physiological effects of the compounds of the present invention are illustrated below in detail.

(1) Effect on mice infected vaccinia virus

Groups, each consisting of 10 ICR female mice weighing about 15 g, were intravenously injected a dilute solution (0.1 ml) of vaccinia virus at a portion 2 cm from the base of a tail. On the 8th day after the inoculation, the number of lesions in the form of small pocks on the tail surface was counted after dyeing the tail with an ethanol solution of 1% fluorescein and 0.5% methylene blue. Each test compound suspended in a surfactant solution was administered intraperitoneally at a rate of 50 mg/kg to the mice 24 hours before inoculation of the virus, whereby antivirus activity of the test compound was evaluated in terms of inhibition of tail lesions as calculated in each test group against a group to which only the surfactant solution had been administered. The rate of tail lesion inhibition of each test compound is shown in Table 3.

TABLE 3

| Test compound | Prevention from vaccinia infection (Pock inhibition rate %) |
|---|---|
| | 57.1 |
| 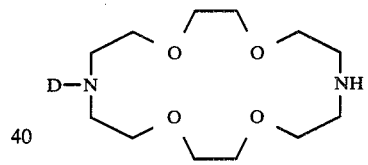 | 60.1 |
|  | 75.5 |
| 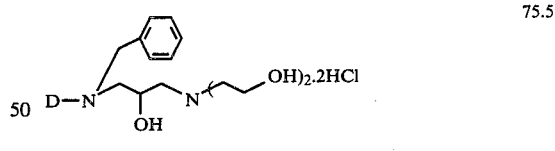 | 60.2 |
| 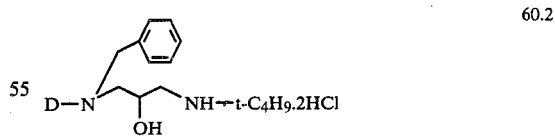 | 82.9 |
| 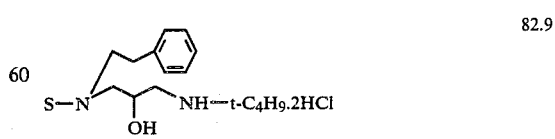 | 85.6 |
| 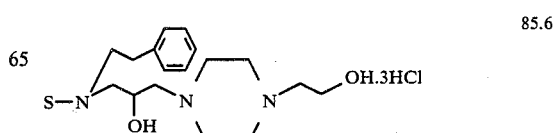 | |

TABLE 3-continued

| Test compound | Prevention from vaccinia infection (Pock inhibition rate %) |
|---|---|
| S—N(CH2Ph)2 .HCl | 50.3 |
| S—N(CH2CH2OH)(CH2Ph) .HCl | 53.4 |
| S2—N-CH2-C6H3(OCH3)2 | 32.4 |
| S2—N-(CH2)3-Ph | 34.1 |
| D2—N-CH2-C6H4-OCH3 | 38.8 |
| D—N(piperazine)-CH2-Ph .2HCl | 64.0 |
| D—N(CH2CH2OH)(CH2Ph) .HCl | 38.4 |
| D2—N-CH2CH2-C6H3(OCH3)2 | 51.3 |

(2) Effect on mice infected with influenza virus

Groups, each consisting of 10 ICR female mice weighing about 25 g were challenged by nasal inhalation of influenza virus (PR-8). Each test compound suspended in a surfactant solution was intraperitoneally administered at a rate of 50 mg/kg to the mice 24 hours before the virus infection, and 5 times every other day from the second day after the infection. The mice that survived 21 days or more after the challenge were regarded as survivors, and survival rate was obtained according to the following equation as shown in Table 4.

$$\left( \frac{\text{Number of survivors of test groups administered test compounds}}{10} - \frac{\text{Number of survivors of test groups administered only surfactant solution}}{10} \right) \times 100 = \text{Survival rate (\%)}$$

TABLE 4

| Test compound | Prevention from influenza infection (Survival rate %) |
|---|---|
| D—N(CH2CH2OH)(CH2CH(OH)Ph) .HCl | 30 |
| D—N(CH2CH(OH)CH2-Ph)(CH2CH2OH)2 .2HCl | 40 |
| D—N(CH2CH(OH)CH2-Ph)(CH2-NH-t-C4H9) .2HCl | 20 |
| S—N(CH2CH(OH)CH2-Ph)(CH2-NH-t-C4H9) .2HCl | 70 |
| S—N(CH2CH(OH)CH2-Ph)(CH2-piperazine-CH2CH2OH) .3HCl | 60 |
| S—N(CH2CH2-C6H4-OH) .HCl | 40 |

(3) Anti-tumor activity

Groups, each consisting of Balb/c male mice weighing about 20 g, were intraperitoneally administered $5 \times 10^5$ of tumor cells $KN_7$-8. Each test compound suspended in a surfactant solution was intraperitoneally administered (each time at a rate of 30 mg/kg) to the mice 24 hours before inoculation of the tumor cells and on the second day and the fifth day after the inoculation, totalling 3 times, and the anti-tumor activity was evaluated in terms of number of survivors on the 30th day after the inoculation. The number of survivors relative to each test compound is shown in Table 5.

TABLE 5

| Test compound | Anti-tumor activity (Survivor on the 30th day) |
|---|---|
| D-N(cryptand with O,O,O,O)NH | 3/6 |

TABLE 5-continued

| Test compound | Anti-tumor activity (Survivor on the 30th day) |
|---|---|
| D-N(CH2CH(OH)CH2N(CH2CH2OH)2)(CH2C6H5) · 2HCl | 1/6 |
| D-N(CH2CH(OH)CH2NH-t-C4H9)(CH2C6H5) · 2HCl | 2/6 |
| S-N(CH2CH(OH)CH2-piperazine-CH2CH2OH)(CH2CH2C6H5) · 3HCl | 4/6 |
| D-N(CH2CH2CH2NH2)2 · 3HCl | 6/6 |
| S-N(CH2CH2CH2NH2)2 · 3HCl | 4/6 |

(4) Toxicity

Using ddY male mice weighing 20–25 g, 50% lethal dose of each test compound when intravenously administered was obtained, the results of which are shown in Table 6.

TABLE 6

| Test compound | LD50 (Intravenous administration mg/kg) |
|---|---|
| D-N(CH2CH(OH)CH(OH)C6H5) · HCl | 258 |
| D-N(CH2CH(OH)CH2N(CH2CH2OH)2)(CH2C6H5) · 2HCl | 162 |

TABLE 6-continued

| Test compound | LD50 (Intravenous administration mg/kg) |
|---|---|
| S-N(CH2CH(OH)CH2NH-t-C4H9)(CH2CH2C6H5) · 2HCl | 28 |
| S-N(CH2CH(OH)CH2-piperazine-CH2CH2OH)(CH2CH2C6H5) · 3HCl | 338 |
| S-N(CH2-C6H4-CH2CH2OH) · HCl | 791 |

(5) Human interferon inducing activity (in vitro)

Interferon was induced according to the method of Edward A. Havell et al. by treating normal diploid cells (fibroblast) originated from human being with each test compound in the form of ethanol solution diluted with PBS (−), (25 n molar suspension). Using the radioisotope microassay method or H. Ishitsuka et al., interferon was measured in terms of 3H-uridine-uptake inhibition rate. The rate of 3H-uridine-uptake inhibition of each test compound as measured is shown in Table 7.

TABLE 7

| Test compound | Human interferon 3H—uridine-uptake inhibition rate (%) |
|---|---|
| D-N(crown ether with O,O,O,O)NH | 28.3 |
| D-N(CH2CH(OH)CH(OH)C6H5) · HCl | 4.3 |
| D-N(CH2CH(OH)CH2N(CH2CH2OH)2)(CH2C6H5) · 2HCl | 61.3 |

TABLE 7-continued

| Test compound | Human interferon 3H—uridine-uptake inhibition rate (%) |
|---|---|
| D-N-CH2-CH(OH)-CH2-NH-t-C4H9·2HCl (benzyl) | 59.8 |
| S-N-CH2-CH(OH)-CH2-NH-t-C4H9·2HCl (phenethyl) | 32.6 |
| S-N-CH2-CH(OH)-CH2-N(piperazine)-CH2CH2OH·3HCl (phenethyl) | 17.4 |
| S-N(dibenzyl)·HCl | 4.4 |
| S-N-CH2-C6H4-CH2OH·HCl | 5.1 |
| S2-N-CH2-C6H3(OCH3)2 | 16.0 |
| S2-N-(CH2)4-C6H5 | 11.8 |
| (Ger)2-N-CH2-C6H3(OCH3)2 | 68.4 |
| D-N(piperazine)-CH2-C6H5·2HCl | 3.6 |
| D-N-CH2-C6H4-CH2CH2OH·HCl | 25.4 |
| D2-N-CH2CH2-C6H4-NH2 | 2.5 |
| D2-N-(CH2)4-C6H5 | 24.0 |
| D2-N-CH2CH2-C6H3(OCH3)2 | 19.2 |

(6) Anti-vaccinia virus activity (in vitro)

Virus plaque-formation inhibition rate of each test compound was obtained by treating vero cells originated from the kidney of African green monkey with the test compound suspension (the compound in the form of ethanol solution was suspended in Hanks culture liquid, 50 n molar concentration) and the virus diluted solution. The inhibition rate of each test compound as measured is shown in Table 8.

TABLE 8

| Test compound | Anti-vaccinia virus activity (Plaque inhibition rate %) |
|---|---|
| D-N-CH2-CH(OH)-CH2-N(-CH2CH2OH)2·2HCl (benzyl) | 10.6 |
| D-N-CH2-C6H4-CH2CH2OH·HCl | 14.1 |

As is clear from the foregoing test results, the active ingredients of the present invention have interferon-inducing activity to vivo and, at the same time, are low in toxicity with showing excellent antiviral activity. In the light of the fact that the strict correlation of interferon activity with the individual antivirus activities is now always observed for the present ingredients, there is considered also a possibility that the antivirus activities of said ingredients at biological level are concerned not only in interferon but also in other defensive mechanism of host. As diseases of human being caused by virus, there are known a number of symptoms, for example, herpes-infected diseases such as herpes simplex, influenza, measles, etc. Accordingly, when the active ingredients of the present invention are used for prevention from virus infection and for the treatment of virus-infected diseases, they are administered to patients by such technique involving oral, inhalant or the like administration as well as subcutaneous, intramuscular and intravenous injection. According to the condition of patient such as age, symptom and route by which the ingredient is administered, the active ingredient of the present invention is used in a dose of 0.5–20 mg/kg, preferably 3–5 mg/kg several times (2–4 times) per day.

The active ingredients of the present invention can be formulated into compositions for medication, for example, tablets, capsules, granules, powder, liquid preparation for oral use, eye lotions, suppositories, ointments, injections and the like.

When the present active ingredients are orally administered, they may be formulated into tablets, capsules, granules or powder. These solid preparations for oral use may contain commonly used excipients, for example, silicic anhydride, metasilicic acid, magnesium alginate, synthetic aluminum silicate, lactose, cane sugar, corn starch, microcrystalline cellulose, hydroxypropylated starch or glycine and the like; and binders, for example, gum arabic, gelatin, tragacanth, hydroxypropyl cellulose, or polyvinyl pyrrolidone; lubricants, for example, magnesium stearate, talc or silica; distintegrating agents, for example, potato starch and carboxymethyl cellulose calcium; or wetting agents, for example, polyethylene glycol, sorbitan monooleate, polyoxyethylene hydrogenated castor oil, sodium lauryl sulfate and the like. In preparing soft capsules, in particular, the present active ingredients may be formulated by dissolving or suspending them in polyethylene glycol or commonly used oily substrates such as sesame oil, peanut oil, germ oil, fractionated coconut oil such as Miglyol ®, or the like. Tablet or granule preparations may be coated according to the usual method.

Liquid preparation for oral use may be in the form of aqueous or oily emulsion or syrup, or alternatively in the form of dry product which can be re-dissolved before use by means of a suitable vehicle. To these liquid preparations, there may be added commonly used additives, for example, emulsifying aids such as sorbitol syrup, methyl cellulose, gelatin, hydroxyethyl cellulose and the like; or emulsifiers, for example, lecithin, sorbitan monooleate, polyoxyethylene hydrogenated castor oil; non-aqueous vehicles, for example, fractionated coconut oil, almond oil, peanut oil and the like; or antiseptics, for example, methyl p-hyroxybenzoate, propyl p-hyroxybenzoate, or sorbic acid. Further, these preparations for oral use may contain, if necessary, preservatives, stabilizers and the like additives.

In case where the present active ingredients are administered in the form of non-oral suppository, they may be formulated according to the ordinary method using oleophilic substrates such as cacao oil or Witepsol ®, or may be used in the form of rectum capsule obtained by wrapping a mixture of polyethylene glycol, sesame oil, germ oil, peanut oil, fractionated coconut oil and the like in a gelatin sheet. The rectum capsule may be coated, if necessary, with waxy materials.

When the present active ingredients are used in the form of injection, they may be formulated into preparations of oil solution, emulsified solution or aqueous solution, and they may contain commonly used emulsifiers, stabilizers or the like additives.

According to the method of administration, the above-mentioned compositions can contain the present active ingredients in an amount of at least 1%, preferably 5 to 50%.

The procedure of formulating the present active ingredients into various preparations is illustrated below with reference to pharmaceutical examples.

Pharmaceutical Example 1

Hard capsule preparations for oral use

A mixture of 25 g of N-(3,4-dimethoxybenzyl)-disolanesylamine and 7.5 g of polyoxyethylene castor oil in acetone was mixed with 25 g of silicic anhydride. After evaporation of the acetone, the mixture was mixed further with 5 g of calcium carboxymethylcellulose, 5 g of corn starch, 7.5 g of hyroxypropylcellulose and 20 g of microcrystalline cellulose, and 30 ml of water was added thereto and kneaded to give a granular mass. The mass was pelletized by means of a pelletizer (ECK pelletizer of Fuji Paudal Co., Japan) equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 190 mg per capsule.

Pharmaceutical Example 2

Soft capsule preparation for oral use

A homogeneous solution was prepared by mixing 50 g of N-(3,4-dimethoxyphenethyl)didecaprenylamine with 130 g of polyethylene glycol (Macrogol 400). Separately, a gelatin solution was prepared which contained 93 g of gelatin, 19 g of glycerin, 10 g of D-sorbitol, 0.4 g of ethyl p-hydroxybenzoate, 0.2 g of propyl p-hydroxybenzoate and 0.4 g of titanium oxide and which was used as a capsule file forming agent. The previously obtained solution, together with the capsule film forming agent, was treated with a manual type flat punching machine to obtain capsules each having the contents of 180 mg.

Pharmaceutical Example 3

Injections

A mixture of 5 g of N-solanesyl-N,N'-(3,4-dimethoxybenzyl)ethylenediamine dihydrochloride, an appropriate amount of peanut oil and 1 g of benzyl alcohol was made a total volume of 100 cc by addition of peanut oil. The solution was portionwise poured in an amount of 1 cc under asepsis operation into an ampule which was then sealed.

Pharmaceutical Example 4

Injections

A mixture of 1.0 g of N-solanesyl-N,N'-dibenzylethylenediamine dihydrochloride, 5.0 g of Nikkol HCO-60 (a trade-name) (hydrogenated castor oil polyoxyethylene-60 mols-ether), 20 g of propylene glycol, 10 g glycerol and 5.0 g of ethyl alcohol was mixed with 100 ml of distilled water and stirred. Under asepsis operation, the solution was portionwise poured in an amount of 1.4 ml into an ampule which was then sealed.

What we claim is:

1. A compound of the formula

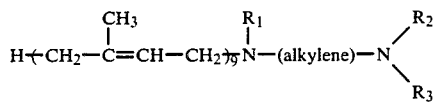

wherein $R_1$ and $R_3$ each is an unsubstituted benzyl group or a benzyl group substituted with up to 3 methoxy groups, $R_2$ is a hydrogen atom, and (alkylene) is a lower alkylene chain; or an acid addition salt thereof.

2. The compound as claimed in claim 1, which is N-solanesyl-N,N'-bis(3,4-dimethoxybenzyl)ethylenediamine dihydrochloride.

3. The compound as claimed in claim 1, which is N-solanesyl-N,N'-dibenzylethylenediamine dihydrochloride.

* * * * *